US00PP15431P3

(12) United States Plant Patent
Westhoff

(10) Patent No.: US PP15,431 P3
(45) Date of Patent: Dec. 14, 2004

(54) ***SCAEVOLA* PLANT NAMED 'WESSCAEDIA'**

(50) Latin Name: *Scaevola aemula*
Varietal Denomination: Wesscaedia

(75) Inventor: Heinrich Westhoff, Südlohn (DE)

(73) Assignee: Josef and Heinrich Westhoff Gartenbau-Spezialkulturen, Sudlohn-Oeding (DE)

( * ) Notice: Subject to any disclaimer, the term of this patent is extended or adjusted under 35 U.S.C. 154(b) by 0 days.

(21) Appl. No.: 10/602,079

(22) Filed: Jun. 23, 2003

(65) Prior Publication Data

US 2004/0143878 P1 Jul. 22, 2004

(51) Int. Cl.[7] ..... A01H 5/00

(52) U.S. Cl. ..... Plt./363

(58) Field of Search ..... Plt./363

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of *Scaevola* plant named Wesscaedia, characterized by its cascading and uniformly rounded plant habit; freely branching plant habit; vigorous growth habit; and numerous white and violet blue bi-colored fan-shaped flowers with white-colored centers.

1 Drawing Sheet

Botanical classification/cultivar designation: *Scaevola aemula* cultivar Wesscaedia.

BACKGROUND OF THE INVENTION

The present Invention relates to a new and distinct cultivar of *Scaevola* plant, botanically known as *Scaevola aemula* and hereinafter referred to by the cultivar name 'Wesscaedia'.

The new cultivar is a whole plant mutation of the *Scaevola* cultivar Fancy, disclosed in U.S. Plant Pat. No. 9,867. The new *Scaevola* was discovered and selected as a single plant in a controlled environment in Vauvert, France in 2000.

Asexual reproduction of the new cultivar by terminal cuttings taken at Sudlohn-Oeding, Germany since 2001, has shown that the unique features of this new *Scaevola* are stable and reproduced true to type in successive generations.

SUMMARY OF THE INVENTION

The new cultivar has not been observed under all possible environmental conditions. The phenotype may vary somewhat with variations in environment such as temperatures, daylength and light intensity, without, however, any variance in genotype.

The following characteristics have been repeatedly observed and are determined to be the basic characteristics of 'Wesscaedia' which distinguish 'Wesscaedia' as a new and distinct cultivar:

1. Cascading and uniformly rounded plant habit.
2. Freely branching habit, dense and bushy plant form.
3. Vigorous growth habit.
4. Numerous white and violet blue bi-colored flowers with white-colored centers.

Plants of the new *Scaevola* can be compared to plants of the parent, the cultivar Fancy. In side-by-side comparisons conducted by the Inventor in Sudlohn-Oeding, Germany, plants of the new *Scaevola* and the cultivar Fancy differed in the following characteristics:

1. Leaves of plants of the new *Scaevola* were darker green in color than leaves of plants of the cultivar Fancy.
2. Plants of the new *Scaevola* were more freely flowering than plants of the cultivar Fancy.
3. Plants of the new *Scaevola* had smaller flowers than plants of the cultivar Fancy.
4. Flowers of plants of the new *Scaevola* were white and violet blue bi-colored whereas flowers of plants of the cultivar Fancy were violet blue in color.

Plants of the new *Scaevola* can also be compared to plants of the cultivar Brilliant, disclosed in U.S. Plant Pat. No. 12,099. In side-by-side comparisons conducted by the Inventor in Sudlohn-Oeding, Germany, plants of the new *Scaevola* and the cultivar Brilliant differed in the following characteristics:

1. Plants of the new *Scaevola* had longer internodes than plants of the cultivar Brilliant.
2. Leaves of plants of the new *Scaevola* were darker green in color than leaves of plants of the cultivar Brilliant.
3. Plants of the new *Scaevola* had more flowers per inflorescence than plants of the cultivar Brilliant.
4. Flowers of plants of the new *Scaevola* were white and violet blue bi-colored with white centers whereas flowers of plants of the cultivar Brilliant were violet blue in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Scaevola*.

The photograph at the top of the sheet comprises a side perspective view of typical plants of 'Wesscaedia'.

The photograph at the bottom of the sheet is a close-up view of a typical inflorescence of 'Wesscaedia'.

DETAILED BOTANICAL DESCRIPTION

Plants used in the aforementioned photographs and for the following description were grown under conditions which closely approximate commercial production conditions during the spring and summer in a glass-covered greenhouse in Sudlohn-Oeding, Germany. Plants were about 20 weeks from planting rooted cuttings in 12-cm containers. During the production of the plants, the day temperatures ranged from 20 to 25° C., night temperatures ranged from 16 to 18° C., and light levels ranged from 3,000 to 50,000 lux. Plants were pinched about three to four weeks after planting and then given a second pinch about four weeks later.

In the following description, color references are made to The Royal Horticultural Society Colour Chart, 2001 Edition, except where general terms of ordinary dictionary significance are used.

Botanical classification: *Scaevola aemula* cultivar Wesscaedia.

Parentage: Mutation of *Scaevola aemula* cultivar Fancy, disclosed in U.S. Plant Pat. No. 9,867.

Propagation:

*Type cutting.*—Terminal cuttings.

*Time to develop roots.*—About four weeks at 22° C.

*Rooting habit.*—Fine, fibrous, and freely branching.

Plant description:

*Plant form and growth habit.*—Annular container and garden plant. Cascading and uniformly mounded plant habit; eventually plants become roughly spherical in shape. Suitable for hanging basket, window box and patio containers. Freely branching with lateral branches potentially forming at every vegetative leaf axil when pinched; dense and bushy plant form. Vigorous growth habit.

*Plant height* (*soil level to top of plant plane*).—About 23 to 26 cm.

*Plant length* (*soil level to apices of lateral branches*).—About 60 to 75 cm.

*Stem description.*—Lateral branch length: About 22 to 29 cm. Lateral branch diameter: About 3.1 mm. Main branch length: About 53 cm. Main branch diameter: About 5.2 mm. Internode length: About 2.6 cm. Texture: Sparsely pubescent. Color: 146B overlain with 166A.

*Foliage description.*—Arrangement: Alternate, simple; sessile. Length: About 5.5 to 8 cm. Width: About 1.5 to 2.8 cm. Shape: Spatulate. Apex: Acute. Base: Attenuate. Margin: Irregularly serrated, slightly serrated towards base and more strongly serrated towards apex. Texture, upper and lower surfaces: Pubescent, rough and somewhat leathery. Color: Developing leaves, upper surface: 147A. Developing leaves, lower surface: 146B. Fully expanded leaves, upper surface: 147A. Fully expanded leaves, lower surface: 146A. Venation, upper surface: 147A. Venation, lower surface: 146A.

Flower description:

*Flower type and shape.*—Zygomorphic, semi-circular, fan-shaped flowers with five petals fused at the base to form a tubular flower throat. Flower throat open along the upper surface exposing reproductive organs. Flowers persistent. No fragrance detected.

*Flower arrangement and quantity.*—Solitary flowers arise from leaf axils with one flower per axil. Flowers held outwardly on upturned lateral apices. Freely flowering, typically about ten to twelve open flowers per inflorescence.

*Flowering time.*—Plants flower continuously from May until frost. Flowers typically last at least four days on the plant.

*Flower buds.*—Shape: Lanceolate. Length: About 5 to 22 mm. Diameter: About 1 to 3 mm. Color: 146C to 146D becoming closer to 145A to 145B with development.

*Perianth.*—Aspect: Fan-shaped, flat. Length, fan: About 3 cm. Width, fan: About 1.6 cm.

*Petals.*—Quantity: Five, fused at base. Shape: Oblanceolate. Apex: Cuspidate. Margin: Entire. Length, above tube: About 1.6 cm. Width, above tube: About 6 mm. Length, tube: About 1.3 cm. Diameter, tube opening: About 4 mm. Diameter, tube: About 2 mm. Texture, upper and lower surfaces: Smooth; flower throat, whiskered. Color: When opening, upper surface: Center, 155D; margins, 90A to 90C. When opening, lower surface and tube: Center, 145A to 155D; margins, 90A to 90C. Fully opened, upper surface: Center, 155D; margins, 90C to 90D; towards base, 155D; venation, 150D. Fully opened, lower surface and tube: Center, 145A to 145D to 155D; margins, 90D; venation, 145A to 145D. Throat: 151A to 151B; venation not visible. Tube: 145C to 160C; venation, 145A.

*Sepals.*—Quantity and arrangement: One large sepal, two smaller sepals lateral to larger sepal. Length: Larger sepal, about 1.36 cm; lateral sepals, about 7 mm. Width: Larger sepal, about 3.6 mm; lateral sepals, about 1 mm. Shape: Larger sepal, lanceolate; lateral sepals, acicular, needle-like. Apex: Acute. Margin: Entire. Texture, upper and lower surfaces: Leathery, slightly pubescent. Color, upper and lower surfaces: 147A.

*Reproductive organs.*—Androecium: Stamen quantity per flower: About five. Anthers: Shape: Oval. Length: About 1.8 mm. Diameter: About 0.5 mm. Color: 11A to 166A. Pollen: Sparse. Pollen color: 166A. Gynoecium: Pistil quantity per flower: One. Pistil length: About 1.6 cm. Style length: About 1.1 cm. Style color: Towards the base, 144D; towards the apex, N79. Stigma shape: Elongate. Stigma color: 155A to 157A. Ovary color: 144A to 144B.

*Seed/fruit.*—Seed and fruit production has not been observed.

Disease/pest resistance: Plants of the new *Scaevola* have been noted to be resistant to pathogens and pests common to *Scaevola*.

Temperature tolerance: Plants of the new *Scaevola* have been observed to be tolerant to temperatures ranging from 2 to 30° C.

It is claimed:

1. A new and distinct *Scaevola* plant named Wesscaedia, as illustrated and described.

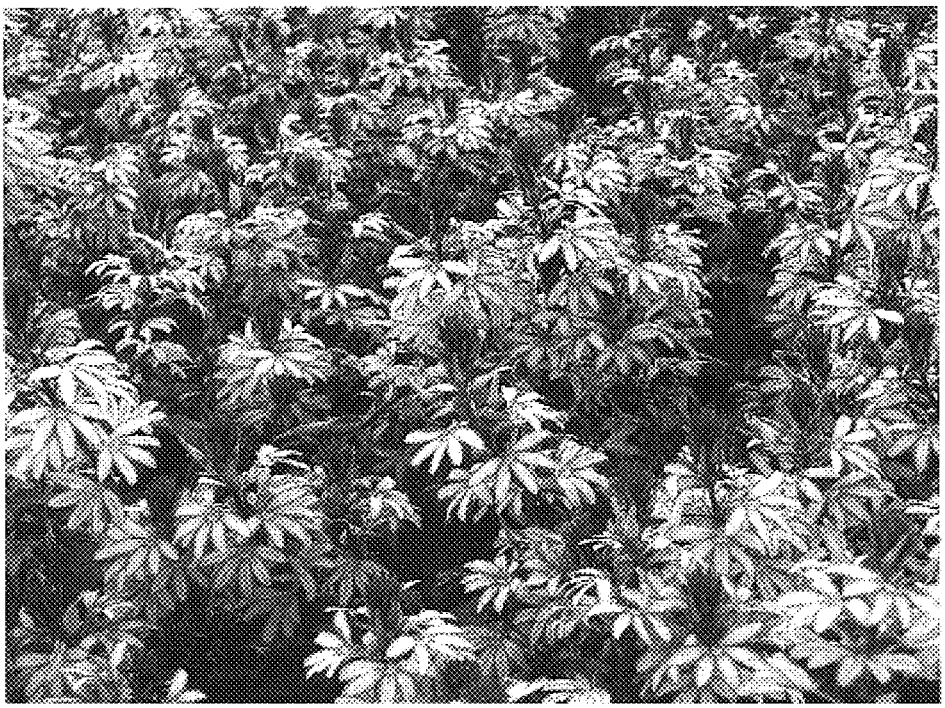
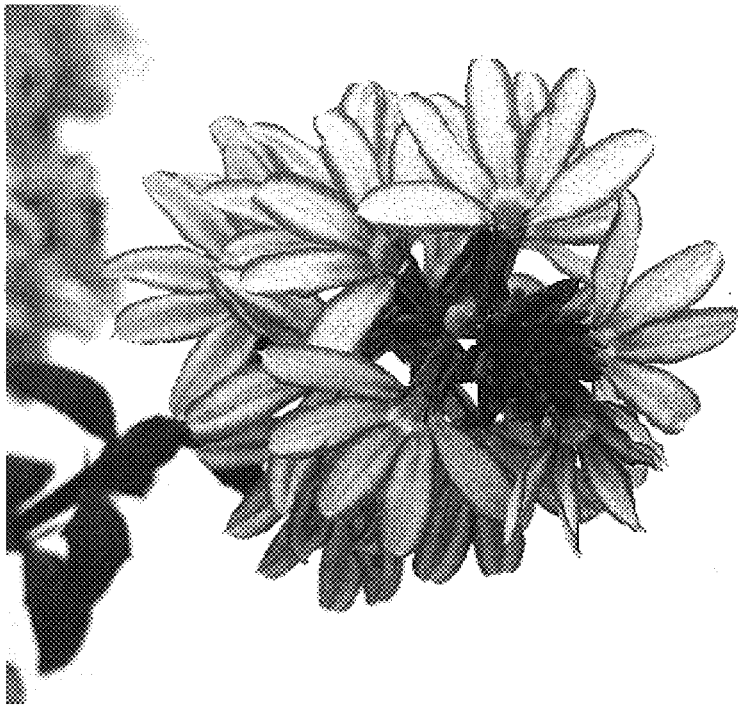

* * * * *